US008577455B2

(12) United States Patent
Mitrani et al.

(10) Patent No.: US 8,577,455 B2
(45) Date of Patent: Nov. 5, 2013

(54) METHOD AND APPARATUS FOR ARRHYTHMIA DETECTION IN A MEDICAL DEVICE

(75) Inventors: Raul D. Mitrani, Hollywood, FL (US); Peter P. Tarjan, Miami, FL (US); Jeffrey M. Gillberg, Coon Rapids, MN (US)

(73) Assignee: Medtronic, Inc., Minneapolis, MN (US)

( * ) Notice: Subject to any disclaimer, the term of this patent is extended or adjusted under 35 U.S.C. 154(b) by 1950 days.

(21) Appl. No.: 11/037,123

(22) Filed: Jan. 18, 2005

(65) Prior Publication Data

US 2006/0161205 A1    Jul. 20, 2006

(51) Int. Cl.
*A61N 1/362* (2006.01)
(52) U.S. Cl.
USPC ....... 607/9; 607/5; 607/27; 607/122; 600/374
(58) Field of Classification Search
USPC .......................................................... 607/2, 5
See application file for complete search history.

(56) References Cited

U.S. PATENT DOCUMENTS

| | | | |
|---|---|---|---|
| 4,349,030 A | 9/1982 | Belgard et al. | 128/419 PG |
| 4,355,642 A | 10/1982 | Alferness | 128/642 |
| 4,587,970 A * | 5/1986 | Holley et al. | 607/15 |
| 4,727,380 A | 2/1988 | Miura et al. | 346/108 |
| 4,727,877 A | 3/1988 | Kallok | 128/419 D |
| 4,800,883 A | 1/1989 | Winstrom | 128/419 D |
| 4,830,006 A | 5/1989 | Haluska et al. | 128/419 PG |
| 4,953,551 A | 9/1990 | Mehra et al. | 128/419 D |
| 5,018,522 A | 5/1991 | Mehra | 128/419 PG |
| 5,117,824 A | 6/1992 | Keimel et al. | 128/419 D |
| 5,161,529 A * | 11/1992 | Stotts et al. | 607/27 |
| 5,163,427 A | 11/1992 | Keimel | 128/419 D |
| 5,188,105 A * | 2/1993 | Keimel | 607/5 |
| 5,193,535 A | 3/1993 | Bardy et al. | |
| 5,257,621 A * | 11/1993 | Bardy et al. | 607/5 |
| 5,275,621 A * | 1/1994 | Mehra | 607/5 |
| 5,295,482 A | 3/1994 | Clare et al. | 128/639 |
| 5,331,966 A * | 7/1994 | Bennett et al. | 600/508 |
| 5,366,486 A * | 11/1994 | Zipes et al. | 607/5 |
| 5,366,487 A | 11/1994 | Adams et al. | |
| 5,388,578 A | 2/1995 | Yomtov et al. | 128/642 |
| 5,520,683 A | 5/1996 | Subramaniam et al. | 606/32 |

(Continued)

FOREIGN PATENT DOCUMENTS

| | | |
|---|---|---|
| EP | 0554208 | 8/1993 |
| EP | 1314450 | 5/2003 |
| WO | WO 2004/043919 A1 | 5/2004 |

OTHER PUBLICATIONS

Besio, W., "A Study of Laplacian Surface Maps From Moments of Activation to Detect Cardiovascular Disease," *Dissertation, University of Miami*, Coral Gables, FL, p. 152 (May 2002).

(Continued)

*Primary Examiner* — Carl H Layno
*Assistant Examiner* — Jon Eric C Morales
(74) *Attorney, Agent, or Firm* — IPLM Group, P.A.

(57) ABSTRACT

A method and device for detecting arrhythmias in a patient that includes electrodes positioned subcutaneously within the patient, a microprocessor, coupled to the electrodes, determining one of a sequence of the sensing of cardiac signals by the electrodes and a duration between the sensing of cardiac signals by the electrodes, and control circuitry delivering a therapy in response to one of the determined sequence and the determined duration.

8 Claims, 9 Drawing Sheets

(56) References Cited

U.S. PATENT DOCUMENTS

| | | | | |
|---|---|---|---|---|
| 5,752,977 | A | 5/1998 | Grevious et al. | 607/32 |
| 5,817,030 | A | 10/1998 | Tarjan et al. | 600/546 |
| 5,891,045 | A | 4/1999 | Albrecht et al. | 600/509 |
| 5,999,857 | A | 12/1999 | Weijand et al. | 607/60 |
| 6,091,977 | A | 7/2000 | Tarjan et al. | 600/372 |
| 6,622,046 | B2 | 9/2003 | Fraley et al. | 607/36 |
| 6,647,292 | B1 | 11/2003 | Bardy et al. | 607/5 |
| 6,745,068 | B2 | 6/2004 | Koyrakh et al. | 600/515 |
| 6,754,528 | B2 | 6/2004 | Bardy et al. | 607/5 |
| 2001/0005792 | A1* | 6/2001 | Steglich | 607/122 |
| 2001/0034539 | A1 | 10/2001 | Stadler et al. | 607/14 |
| 2002/0035377 | A1 | 3/2002 | Bardy et al. | 607/4 |
| 2002/0035381 | A1 | 3/2002 | Bardy et al. | 607/4 |
| 2002/0042634 | A1 | 4/2002 | Bardy et al. | 607/36 |
| 2002/0052636 | A1 | 5/2002 | Bardy et al. | 607/129 |
| 2002/0068958 | A1 | 6/2002 | Bardy et al. | 607/5 |
| 2002/0082658 | A1 | 6/2002 | Heinrich et al. | 607/9 |
| 2002/0091414 | A1 | 7/2002 | Bardy et al. | 607/4 |
| 2003/0236466 | A1 | 12/2003 | Tarjan et al. | 600/508 |
| 2004/0220633 | A1* | 11/2004 | Wagner et al. | 607/9 |

OTHER PUBLICATIONS

Kaufer, Monica, "Multi-Ring Sensing Electrodes for Arrhythmia Detection and Classification," *Thesis, University of Miami*, Coral Gables, FL, p. 1-86 (Jun. 1992).

Lu, Chih-Cheng, "Non-Invasive Laplacian ECG Detection Using Active Concentric Ring Sensors," *Dissertation, University of Miami*, Coral Gables, FL, p. 1-138 (Jun. 1998).

Rasquinha, L., "Classification of Arrhythmias Using Specialized Concentric Ring Electrodes," *Thesis, University of Miami*, Coral Gables, FL, p. 1-168 (Dec. 1993).

* cited by examiner

|  | NSR | RHYTHM |
|---|---|---|
| ELECTRODE 204 | 0 ms —800 | 80 ms —808 |
| ELECTRODE 210 | 80 ms —804 | 0 ms —806 |
| ELECTRODE 211 | 30 ms —802 | 130 ms —810 |

METHOD AND APPARATUS FOR ARRHYTHMIA DETECTION IN A MEDICAL DEVICE

FIELD OF THE INVENTION

The present invention relates generally to medical devices, and, more particularly, to a method and apparatus for sensing and detecting arrhythmias in a medical device.

BACKGROUND OF THE INVENTION

Implantable medical devices (IMDs) have many functions including the delivery of therapies to cardiac patients, neurostimulators, muscular stimulators, and others. For purposes of this application reference will be made only to implantable cardiac devices, it being understood that the principles herein may have applicability to other implantable medical devices as well.

An implantable cardiac device (ICD) may be a device commonly referred to as a pacemaker, which is used to stimulate the heart into a contraction if the sinus node of the heart is not properly timing, or pacing, the contractions of the heart. Modern cardiac devices also perform many other functions beyond that of pacing. For example, some cardiac devices may also perform therapies such as defibrillation and cardioversion as well as providing several different pacing therapies, depending upon the needs of the user and the physiologic condition of the user's heart. For convenience, all types of implantable cardiac devices will be referred to herein as ICDs, it being understood that the term, unless otherwise indicated, is inclusive of an implantable device capable of administering any of a number of therapies to the heart of the user.

In typical use, an ICD is implanted in a convenient location usually under the skin of the user and in the vicinity of the one or more major arteries or veins. One or more electrical leads connected to the pacemaker are inserted into or on the heart of the user, usually through a convenient vein or artery. The ends of the leads are placed in contact with the walls or surface of one or more chambers of the heart, depending upon the particular therapies deemed appropriate for the user.

One or more of the leads is adapted to carry a current from the pacemaker to the heart tissue to stimulate the heart in one of several ways, again depending upon the particular therapy being delivered. The leads are simultaneously used for sensing the physiologic signals provided by the heart to determine when to deliver a therapeutic pulse to the heart, and the nature of the pulse, e.g., a pacing pulse or a defibrillation shock.

There has been recent interest in development of implantable defibrillators that may be inserted entirely subcutaneously or sub-muscularly, having no leads or electrodes within the thoracic cavity. The elimination of transvenous or epicardial leads is believed likely to allow for implant of the devices by a wider range of physicians, in some cases at a lower cost than traditional ICDs. Absence of transvene or epicardial leads may reduce acute and long term complications. Such devices, are therefore believed to offer the opportunity for increased levels of use, particularly for prophylactic implant. US Application Publication Nos. 2002/0042634, 200200068958 and 2002/0035377 to Bardy et al., are exemplary of current thinking with regard to such subcutaneous ICDs. Additional subcutaneous ICDs are disclosed in US Application Publication No. 20020082658 by Heinrich et al. and PCT publication WO/04043919A2 by Olson. All of the above cited applications and publications are incorporated herein by reference in their entireties.

One potential problem associated with the sensing of the physiologic signal from the heart in both the transvenous systems and the subcutaneous systems relates to what is often referred to as "false positive" and "false negative" detections. The most widely accepted detection algorithm is based on the rate of depolarizations of the ventricles, or simply on "heart rate". Such algorithms rely on detecting events based upon signals obtained between two electrodes positioned within or on the heart. If the number of detected events per a given time is greater than a preset value, then the device charges an energy storage capacitor and then shocks the heart; otherwise no shock is delivered.

BRIEF DESCRIPTION OF THE DRAWINGS

Aspects of the present invention will be readily appreciated as they become better understood by reference to the following detailed description when considered in connection with the accompanying drawings, wherein.

DETAILED DESCRIPTION OF THE INVENTION

Figure 1:
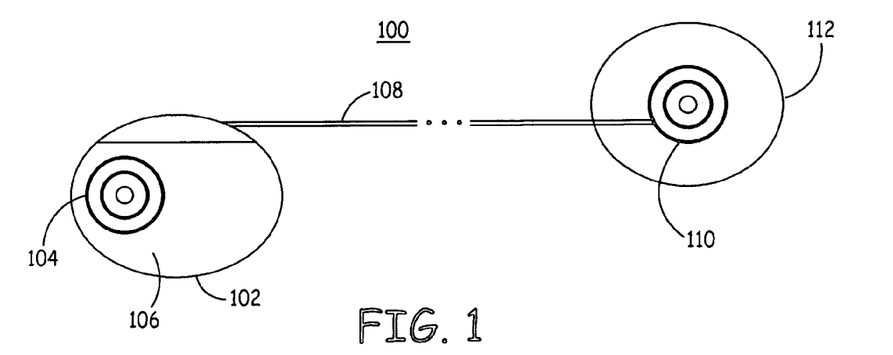
FIG. 1 is a schematic diagram of an exemplary medical device according to the present invention.

FIG. 1 is a schematic diagram of an exemplary medical device according to the present invention. As illustrated in FIG. 1, a medical device 100 according to an embodiment of the present invention, which may be an implantable cardioverter/defibrillator (ICD), for example, includes a housing 102 having an electrode 104 positioned along a side wall 106 of housing 102 that is intended to be directed inward towards a heart of a patient when housing is positioned subcutaneously within the patient, as will be described in detail below. Housing 102 is coupled to a subcutaneous lead 108 carrying conventional conductors (not shown) extending therethrough to electrically couple circuitry located within housing 102 to an electrode 110 positioned on an insulated patch 112 positioned subcutaneously within the patient so that electrode 110 is directed towards the patient's heart.

According to the present invention, electrodes 104 and 110 are formed using Laplacian electrodes that are utilized both as sensors to sense cardiac depolarization signals and as high voltage cardioversion/defibrillation electrodes to deliver cardioversion/defibrillation therapy to the patient. Since the sensitivity of Laplacian sensors to events, especially to dipole layers corresponding to the depolarization of the heart, decreases with the inverse distance cube ($1/r^3$), electrodes 104 and 110 sense signals in a very localized and reduced area, resulting in larger cardiac signal to noise ratios than in conventional sensing methodologies. In addition, because of the reduced sensing area, noise due to body motion will only intermittently affect signal quality when local muscles are activated during the body motion.

Figure 2:
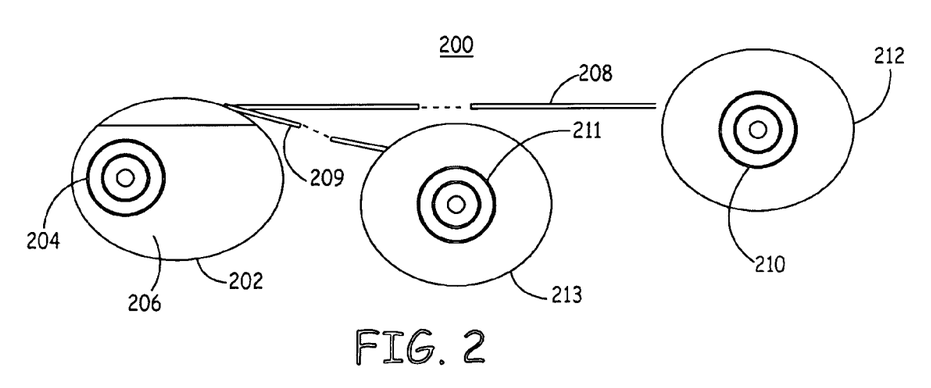
FIG. 2 is a schematic diagram of an exemplary medical device according to the present invention.

FIG. 2 is a schematic diagram of an exemplary medical device according to the present invention. As illustrated in FIG. 2, a medical device 200 according to another embodiment of the present invention includes a housing 202 having an electrode 204 positioned along a side wall 206 of housing 202 that is intended to be directed inward towards the heart of a patient when housing 202 is positioned subcutaneously within the patient. Housing 202 is coupled to two subcutaneous leads 208 and 209, each carrying conventional conductors (not shown) extending therethrough to electrically couple circuitry located within housing 202 to respective electrodes 210 and 211 positioned on associated insulated patches 212 and 213 that are to be positioned subcutaneously within the patient so that electrodes 210 and 211 are directed towards the patient's heart.

Figure 3:
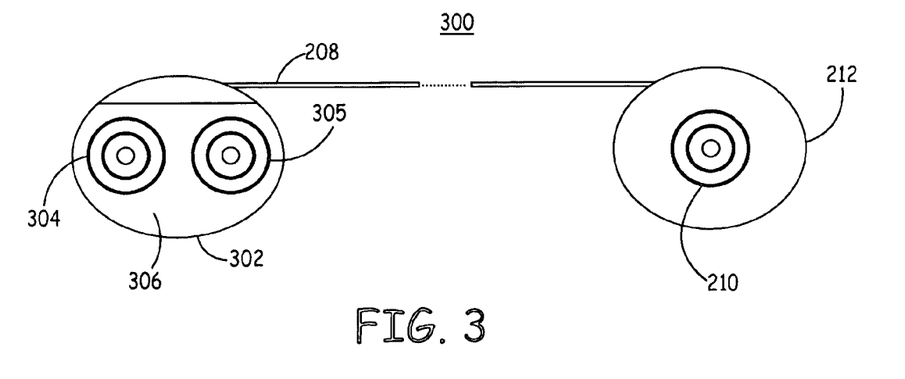
FIG. 3 is a schematic diagram of an exemplary medical device according to the present invention.

FIG. 3 is a schematic diagram of an exemplary medical device according to the present invention. As illustrated in FIG. 3, a medical device 300 according to the present invention may include a housing 302 having two electrodes 304 and 305 positioned along a side wall 306 of housing 302 that is intended to be directed inward towards the heart of a patient when housing 302 is positioned subcutaneously within the patient. Housing 302 is coupled to a subcutaneous lead 208 carrying conventional conductors (not shown) extending therethrough to electrically couple circuitry located within housing 302 to an electrode 210 positioned on an insulated patch 212 that is intended to be positioned subcutaneously within the patient so that electrode 210 is directed towards the patient's heart.

Figure 4:
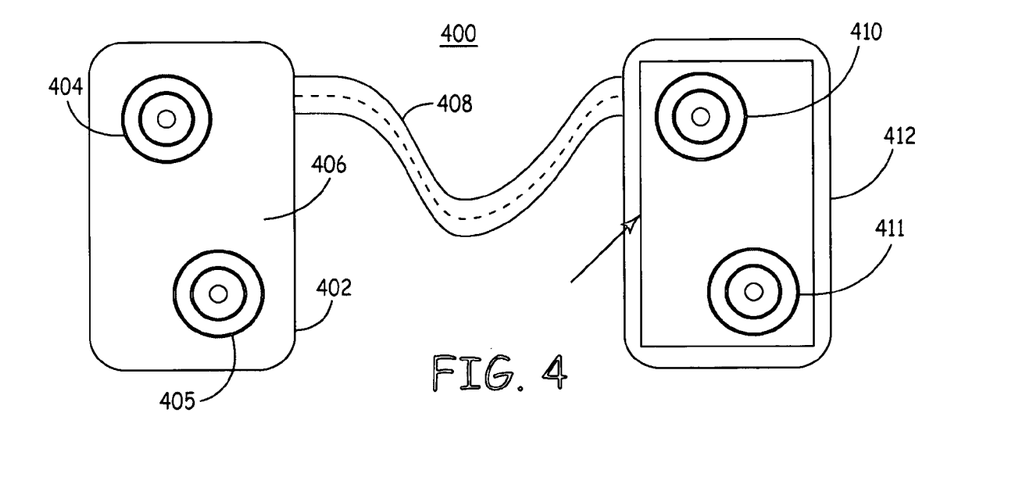
FIG. 4 is a schematic diagram of an exemplary medical device according to the present invention.

FIG. 4 is a schematic diagram of an exemplary medical device according to the present invention. As illustrated in FIG. 4, a medical device 400 according to the present invention may include a housing 402 having two electrodes 404 and 405 positioned along a side wall 406 of housing 402 that is intended to be directed inward towards the heart of a patient when housing 402 is positioned subcutaneously within the patient. Housing 402 is coupled to subcutaneous leads 408 and 409, each carrying conventional conductors (not shown) extending therethrough to electrically couple circuitry located within housing 402 to electrodes 410 and 411 positioned on a second housing 412 that is intended to be positioned subcutaneously within the patient so that electrodes 410 and 411 are directed towards the patient's heart. According to yet another embodiment, electrodes 410 and 411 are positioned on an insulated patch 412 so that housing 402 is coupled to insulated patch 412 via leads 408 and 409.

Figure 5:
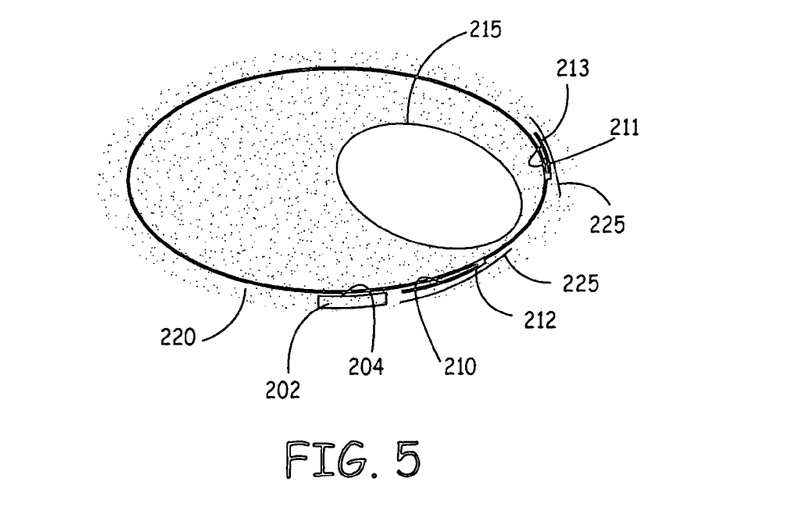
FIG. 5 is a top cross sectional view illustrating the positioning of a medical device according to an embodiment of the present invention.

FIG. 5 is a top cross sectional view illustrating the positioning of a medical device according to an embodiment of the present invention. It is understood that the present invention is not intended to be limited to the exemplary electrode configurations of FIGS. 1-4. Rather, any desired number of electrodes may be located on the housing and any number of insulated patches containing any number or array of electrodes may be coupled to the housing via corresponding leads. In addition, the electrodes may be utilized only for pacing and/or only for sensing without departing from the invention. Furthermore, placement of the housing and electrodes will depend upon the number of electrodes utilized.

For example, as illustrated in FIG. 5, in the three electrode embodiment of the present invention illustrated in FIG. 2, housing 202 is positioned along side of costal muscle 220 along the abdomen below the sternum so that electrode 204 positioned along side wall 206 of housing 202 is directed inward towards the heart 215 of a patient. According to the present invention, housing 202 may or may not include one or more electrodes, as described above. In addition, one insulated patch 212 is positioned in the anterior thorax, overlaying the heart, slightly left of the sternum and within the fourth intercostal space to be positioned at a location associated the V4 lead of the twelve-lead ECG position so that electrode 210 is directed inward towards heart 215. The other insulated patch 213 is positioned laterally left of the sternum from insulated patch 212 to be located at the V6 lead location of the twelve-lead ECG position so that electrode 211 is directed inward towards heart 215. In this way, electrodes 210 and 211 are positioned so that a vector extending between electrodes 210 and 211 extends through an appropriate portion of heart 215.

Figure 6:
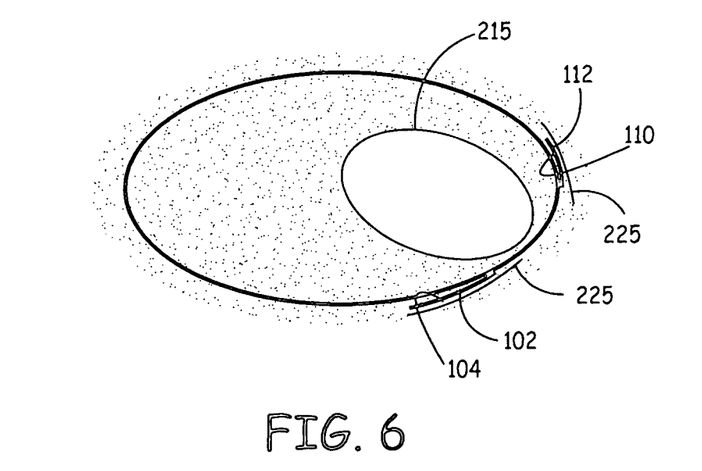
FIG. 6 is a top cross sectional view illustrating the positioning of a medical device according to an embodiment of the present invention.

FIG. 6 is a top cross sectional view illustrating the positioning of a medical device according to an embodiment of the present invention. As illustrated in FIGS. 1 and 6, in the two electrode embodiment of the present invention, housing 102 is positioned in the anterior thorax, overlaying the heart, slightly left of the sternum and within the fourth intercostal space to be positioned at a location associated the V4 lead of the twelve-lead ECG position so that electrode 104 is directed inward towards heart 215. Insulated patch 112 is positioned laterally left of the sternum from housing 102 to be located at the V6 lead location of the twelve-lead ECG position so that electrode 110 is directed inward towards heart 215. In this way, electrodes 104 and 110 are positioned so that a vector extending between electrodes 104 and 110 extends through an appropriate portion of heart 215.

According to the present invention, an insulated layer 225 may be included along an outer portion of the insulated patches in order to reduce the effects of the current delivered from the electrodes on subcutaneous nerves along electrodes, resulting in a reduction of pain that may be experienced by the patient during delivery of cardioversion/defibrillation therapy by the medical device.

Figure 7:
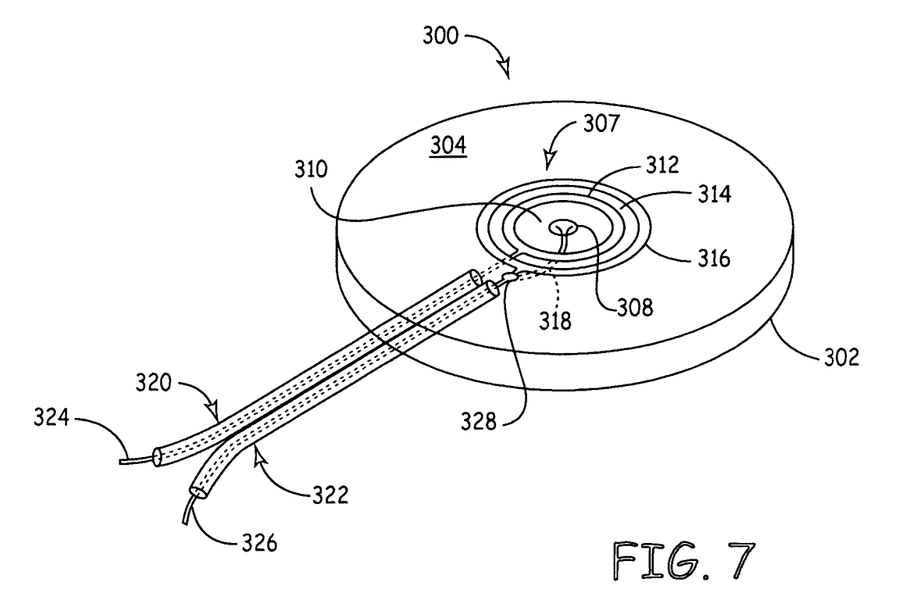
FIG. 7 is a schematic view of a sensor of a medical device according the present invention.

FIG. 7 is a schematic view of a sensor of a medical device according the present invention. As illustrated in FIG. 7, an electrode 300 of the present invention, such as any of the electrodes described above, includes a disk-shaped, electrically insulating patch 302 formed of silicone rubber or other compliant, electrically insulating material. Insulating patch 302 defines a generally planar contact surface 304 into which an electrically conductive sub-assembly 307 is substantially flushly embedded. Sub-assembly 307 includes an electrically conductive inner pad 308 separated by a first insulating layer 310 from a continuous middle loop electrode 312. Loop electrode 312 is surrounded by a second insulating layer 314, which, in turn, is surrounded by a continuous exterior loop electrode 316. In order to provide electrode 300 with uniform directionality of response in a plane during sensing, inner pad 308 is round and circular in shape and loop electrodes 312 and 316 are formed as circular rings located concentrically with respect to pad 308 as well as with respect to one another. In applications where uniform directionality of response is not required or where it is desired to provide enhanced or reduced sensitivity in certain directions, pad 308 and/or loop electrodes 312 and 316 can be formed in other shapes and/or located off center with respect to one another provided that at least some mutual spacing is maintained between pad 308 and continuous loop electrodes 312 and 316.

In order to render electrode 300 sensitive only to the electrical activity of that muscle tissue which substantially immediately underlies the skin surface which sub-assembly 307 is placed in contact with, inner pad 308 and electrode 316 are electrically coupled to one another, preferably by a short circuit. For example, this is achieved by a jumper wire 318 having one end connected to pad 308 and its opposing end connected to electrode 316. The portion of jumper wire 318 that crosses electrode 312 is electrically insulated in order to electrically isolate electrode 312 from both pad 308 and electrode 316. Electrode 300 is provided with a pair of insulated lead wires 320, 322. A conductor 324 extending through lead wire 320 is connected directly to electrode 312 while a conductor 326 extending through lead wire 322 is connected electrically in common with both inner pad 308 and electrode 316. This is conveniently accomplished with a single electrical connection 328 by attaching the conductor 326 of lead wire 322 directly to jumper wire 318. To avoid detachment of lead wires 320 and 322 from sub-assembly 307, strain relief is preferably provided by anchoring wires 320 and 322 to patch 302. This may readily be achieved by insert molding or use of an adhesive. Concentricity of pad 308 and electrodes 312 and 316 may be assured by various means, molding or performing patch 302 with a recess for locating pad 308 and appropriately sized and centered channels for receiving electrodes 312 and 316.

Although a single pad and two concentric rings are shown in FIG. 7, it is understood that other configurations are intended to be included in subcutaneous sensing and detecting according to the present invention. For example, sensor 300 may include inner pad 308 and a single concentric electrode 316, thus eliminating the need for electrode 312, insulating layer 314 and jumper wire 318. The benefit of such a bi-polar configuration is that it provides increased signal amplitudes, although the signal localization may be reduced.

As the distance between the electrodes 312 and 316 increases, or in the bi-polar configuration, as the distance between pad 308 and electrode 316 increases, the amplitude of the detected signal increases, and the sensor 300 becomes more sensitive to sources further away from the immediate vicinity of the electrode 300. Although the desired total radius of the sub-assembly 307 associated with the sensor typically will be dependent on the patient's anatomy, the inventors have found that a for a person of median anatomy, sub-assembly 307 should be approximately between 10 mm and 70 mm in diameter, for example. According to an embodiment of the present invention, sub-assembly 307 is approximately 35 mm in diameter. In one embodiment, a distance 330 between electrodes 312 and 316, in which insulating layer 314 is located, is approximately equal to 2 mm, although distance 330 could have any desired value, depending upon the level of far-field sensitivity desired.

It is understood that while patch 302 is shown having a circular shape, the present invention is not intended to be limited to the use of circular patches and electrodes. Rather, the patch may be formed in any shape, including oval, square, rectangular and so forth. In addition, while electrodes 312 and 316 are shown as being concentric and circular, they may have other desired shapes without departing from the present invention.

Figure 8:
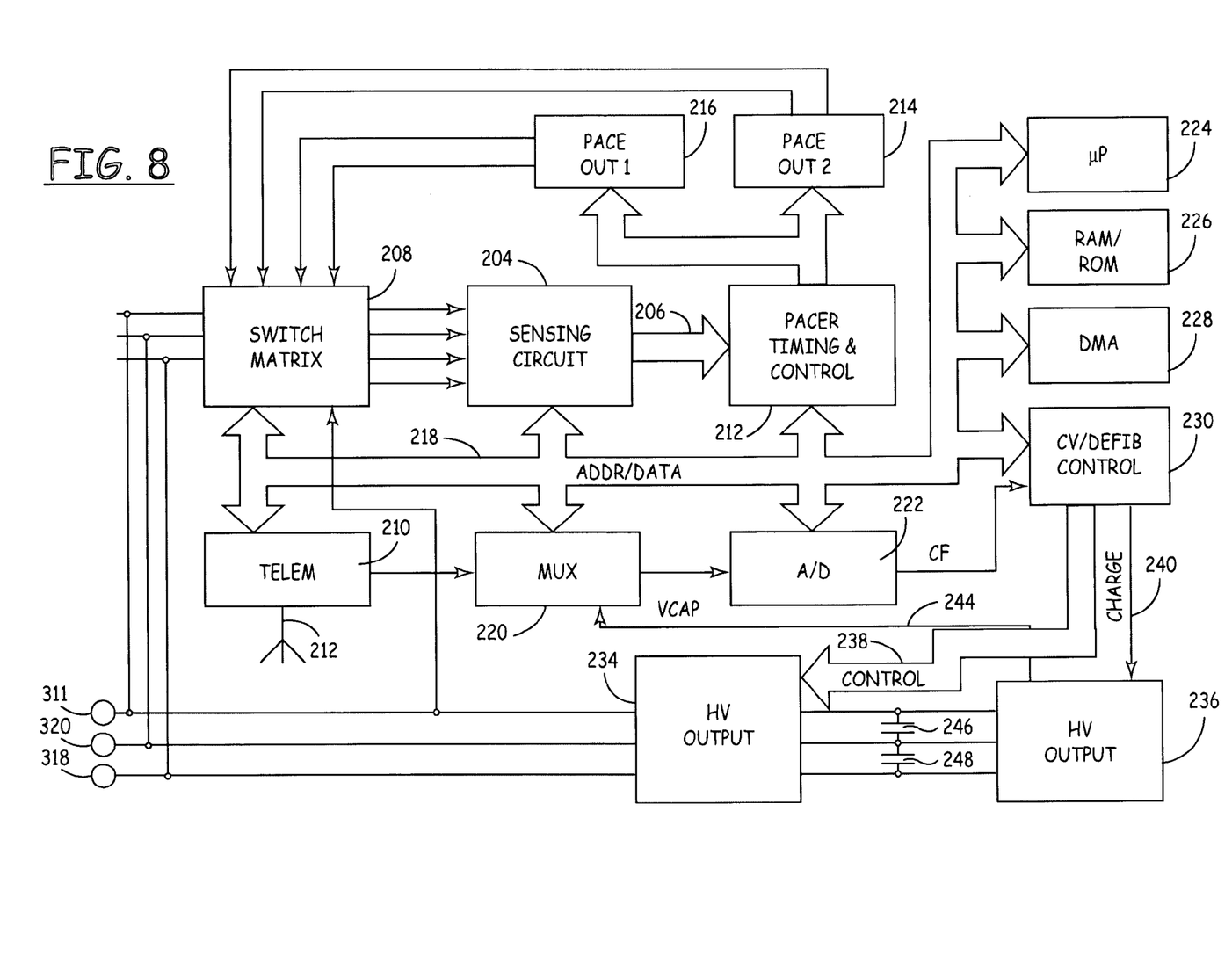
FIG. 8 is a functional schematic diagram of an implantable pacemaker/cardioverter/defibrillator (ICD) in which the present invention may usefully be practiced.

FIG. 8 is a functional schematic diagram of an implantable pacemaker/cardioverter/defibrillator (ICD) in which the present invention may usefully be practiced. This diagram should be taken as exemplary of the type of device in which the invention may be embodied, and not as limiting, as it is believed that the invention may usefully be practiced in a wide variety of device implementations, including devices providing therapies for treating atrial arrhythmias instead of or in addition to ventricular arrhythmias, pacemakers which do not provide anti-tachycardia pacing therapies, anti-tachycardia pacers which do not provide cardioversion or defibrillation, and totally subcutaneous devices that deliver defibrillation and/or pacing therapies or subcutaneous monitoring-only devices that do not provide therapy. Most of the components of the ICD as illustrated correspond to those used in prior art Medtronic implantable defibrillators. In particular, reference is made to US Patent Publication No. 20020082658 to Heinrich et al. and PCT Publication No. WO/04043919A2 to Olson, as well as to US Patent Application Publication No. 20010034539 by Olson et al., all incorporated herein by reference in their entireties. While the circuitry described above is based upon implantable device circuitry, similar circuitry would be used in those embodiments in which the invention is practiced as an external pacemaker or defibrillator, coupled to a subcutaneous electrode array according to the present invention.

The device is provided with electrodes, which may be as described above. Alternate lead systems embodying the invention may also be substituted. The functions of the illustrated electrodes are as follows: Electrode 311 is a first defibrillation/cardioversion electrode and corresponds to electrodes 104, 204, 304, 404 and 408, located on the device housings, for example. Electrode 320 is a second cardioversion/defibrillation electrode and corresponds to the lead mounted cardioversion/defibrillation electrodes 110, 210, 410, 411, for example. Electrode 318 corresponds to the optional third defibrillation electrode referred to in conjunction with FIGS. 2-4. As such, there may be more or less than the three electrodes illustrated, which are intended to merely be exemplary.

Electrodes 311, 318 and 320 are coupled to high voltage output circuit 234 and switch matrix 208, which under control of microprocessor 224 selectively couples electrodes 311, 318 and 320 to sensing circuit 204 and/or to pacing output circuits 216 and 214. Sensing circuit 204 preferably takes the form of one or more automatic gain controlled amplifiers providing adjustable sensing threshold as a function of the measured depolarization wave amplitudes. A signal is provided to pacer timing and control circuitry 212 when a sensed signal or signals indicate occurrence of a cardiac depolarization. The general operation of the sensing circuit 204 may correspond to that disclosed in U.S. Pat. No. 5,117,824, to Keimel et al., incorporated herein by reference in its entirety. Amplifier gain would have to be increased as compared to devices employing electrodes directly contacting the heart. Alternatively, amplifiers more closely resembling those discussed in the Heinrich et al. application cited above or in automatic external defibrillators might be substituted.

Signals from sensing circuit 204 may also be provided to multiplexer 220, and thereafter converted to multi-bit digital signals by A/D converter 222, for storage in RAM/ROM 226 under control of direct memory access circuit 228. Microprocessor 224 may employ digital signal analysis techniques to characterize the digitized signals stored in random access memory 226 to recognize and classify the patient's heart rhythm employing any of the numerous signal processing methodologies known to the art.

Control of the ICD by the physician or by a patient is accomplished via telemetry circuit 210. Externally generated programming signals are received by antenna 212, demodulated by telemetry circuitry 210 and passed through multiplexer 220 to the microprocessor via bus 218. The telemetry circuitry may be any conventional telemetry circuit employed in prior art implantable pacemakers and defibrillators and may correspond to that described in U.S. Pat. No. 5,752,977 issued to Grevious, et al. or to U.S. Pat. No. 5,999,857 issued to Weijand, et al, both of which are included by reference in their entireties.

The remainder of the circuitry is dedicated to the provision of cardiac pacing, cardioversion and defibrillation therapies, and, for purposes of the present invention may correspond generally to circuitry known in the prior art. An exemplary apparatus is disclosed of accomplishing pacing, cardioversion and defibrillation functions follows. The pacer timing/control circuitry 212 includes programmable digital counters which control the basic rime intervals associated—with single chamber anti-bradycardia pacing, typically ventricular pacing. Circuitry 212 also controls escape intervals associated with single chamber anti-tachyarrhythmia pacing, also typically ventricular pacing, employing any antitachyarrhythmia pacing therapies known to the art. Alternative embodiments in which atrial cardioversion/defibrillation and/or atrial anti-tachycardia pacing are also believed to be within the scope of the invention.

Intervals defined by pacing circuitry 212 typically include ventricular pacing escape intervals, the refractory periods during which sensed P-waves and R-waves are ineffective to restart timing of the escape intervals and the pulse widths of the pacing pulses. The durations of these intervals are determined by microprocessor 224, in response to stored data in memory 226 and are communicated to the pacing circuitry 212 via address/data bus 218. Pacer circuitry 212 also determines the amplitude of the cardiac pacing pulses under control of microprocessor 224.

During pacing, the escape interval counters within pacer timing/control circuitry 212 are typically reset upon sensing of R-waves as indicated by signals on bus 206, and in accordance with the selected mode of pacing on timeout trigger generation of pacing pulses by pacer output circuits 214 and/or and 216, which are coupled to electrodes 311, 318 and 320. Output circuits 214 and 216 may correspond to conventional cardiac pacing output circuits, with the exception that they provide pulses of higher amplitude, e.g. up to 20 volts or higher or up to 35 milliamps or higher. Alternatively, output circuits 214 and 216 may correspond generally to that disclosed in U.S. Pat. No. 4,349,030 issued to Belgard et al., which employs a long duration pacing pulse to reduce pain associated with transcutaneous pacing or to that disclosed in U.S. Pat. No. 5,018,522 issued to Mehra, which employs a ramped pacing pulse to reduce pain associated with transcutaneous pacing. Output circuits 214 and/or 216 may also provide pacing pulses of different amplitudes to different pairs or sets of electrodes, under control of microprocessor 224 in conjunction with other electrode configurations employing multiple electrode pairs.

The escape interval counters are also reset on generation of pacing pulses, and thereby control the basic timing of cardiac pacing functions, including anti-tachyarrhythmia pacing. The durations of the intervals defined by the escape interval timers are determined by microprocessor 224, via data/address bus 218. The value of the count present in the escape interval counters when reset by sensed R-waves and P-waves may be used to measure the durations of R-R, which measurements are stored in memory 226 and used in conjunction with the present invention to diagnose the occurrence of a variety of tachyarrhythmias Microprocessor 224 operates as an interrupt driven device, and is responsive to interrupts from pacer timing/control circuitry 212 corresponding to the occurrences of sensed R-waves and corresponding to the generation of cardiac pacing pulses. These interrupts are provided via data/address bus 218. Any necessary mathematical calculations to be performed by microprocessor 224 and any updating of the values or intervals controlled by pacer timing/control circuitry 212 take place following such interrupts. A portion of the memory 226 may be configured as a plurality of recirculating buffers, capable of holding series of measured intervals, which may be analyzed in response to the occurrence of a pace or sense interrupt to determine whether the patient's heart is presently exhibiting ventricular tachyarrhythmia.

In the event that a ventricular tachyarrhythmia is detected, and an anti-tachyarrhythmia pacing regimen is desired, appropriate timing intervals for controlling generation or anti-tachyarrhythmia pacing therapies are loaded from microprocessor 224 into the pacer timing and control circuitry 212, to control the operation of the escape interval counters therein and to define refractory periods during which detection of R-waves and P-waves is ineffective to restart the escape interval counters.

In the event that generation of a cardioversion or defibrillation pulse is required, microprocessor 224 employs the escape interval counter to control timing of such cardioversion and defibrillation pulses, as well as associated refractory periods. In response to the detection of atrial or ventricular fibrillation or tachyarrhythmia requiring a cardioversion pulse, microprocessor 224 activates cardioversion/defibrillation control circuitry 230, which initiates charging of the high voltage capacitors 246, 248 via charging circuit 236, under control of high voltage charging control line 240. The voltage on the high voltage capacitors is monitored via VCAP line 244, which is passed through multiplexer 220 and in response to reaching a predetermined value set by microprocessor 224, results in generation of a logic signal on Cap Full (CF) line 254, terminating charging. Thereafter, timing of the delivery of the defibrillation or cardioversion pulse is controlled by pacer timing/control circuitry 212. Following delivery of the fibrillation or tachycardia therapy the microprocessor then returns the device to cardiac pacing and awaits the next successive interrupt due to pacing or the occurrence of a sensed atrial or ventricular depolarization.

One embodiment of an appropriate system for delivery and synchronization of ventricular cardioversion and defibrillation pulses and for controlling the timing functions related to them is disclosed in more detail in commonly assigned U.S. Pat. No. 5,188,105 to Keimel, incorporated herein by reference in its entirety. However, any known cardioversion or defibrillation pulse control circuitry is believed usable in conjunction with the present invention. In the illustrated device, delivery of the cardioversion or defibrillation pulses is accomplished by output circuit 234, under control of control circuitry 230 via control bus 238. Output circuit 234 determines whether a monophasic or biphasic pulse is delivered, whether the housing serves as cathode or anode and which electrodes are involved in delivery of the pulse. An example of output circuitry for delivery of biphasic pulse regimens may be found in U.S. Pat. No. 4,727,877 to Kallok, incorporated by reference in its entirety.

An example of circuitry which may be used to control delivery of monophasic pulses is set forth in commonly assigned U.S. Pat. No. 5,163,427, by Keimel, issued Nov. 17, 1992, also incorporated herein by reference in its entirety. However, output control circuitry as disclosed in U.S. Pat. No. 4,953,551, issued to Mehra et al. on Sep. 4, 1990 or U.S. Pat. No. 4,800,883, issued to Winstrom on Jan. 31, 1989 both incorporated herein by reference in their entireties, may also be used in conjunction with a device embodying the present invention for delivery of biphasic pulses.

In modern implantable cardioverter/defibrillators, the particular therapies are programmed into the device ahead of time by the physician, and a menu of therapies is typically provided. For example, on initial detection of a tachycardia, an anti-tachycardia pacing therapy may be selected and delivered to the pacing electrode array. On redetection of tachycardia, a more aggressive anti-tachycardia pacing therapy may be scheduled. If repeated attempts at anti-tachycardia pacing therapies fail, a higher level cardioversion pulse may be selected thereafter. Therapies for tachycardia termination may also vary with the race of the detected tachycardia, with the therapies increasing in aggressiveness as the rate of the detected tachycardia increases. For example, fewer attempts at antitachycardia pacing may be undertaken prior to delivery of cardioversion pulses if the rate of the detected tachycardia is above a preset threshold. The references cited above in conjunction with descriptions of prior art tachycardia detection and treatment therapies are applicable here as well.

In the event that fibrillation is identified, the typical therapy will be delivery of a high amplitude defibrillation pulse, typically in excess of 5 joules. Lower energy levels may be employed for cardioversion. As in the case of currently available implantable pacemaker/cardioverter/defibrillators, and as discussed in the above-cited references, it is envisioned that the amplitude of the defibrillation pulse may be incremented in response to failure of an initial pulse or pulses to terminate fibrillation. Prior art patents illustrating such preset therapy menus or anti-tachyarrhythmia therapies include U.S. Pat. No. 4,830,006, issued to Haluska et al., U.S. Pat. No. 4,727,380, issued to Vollmann et al. and U.S. Pat. No. 4,587,970, issued to Holley et al., all also incorporated herein by reference in their entireties.

The device illustrated in FIG. 8 provides the full functionality of a modern ICD. If the invention is to be practiced in an embodiment wherein no high voltage cardioversion/defibrillation pulses are to be delivered, such in cases in which the pacing electrode array is coupled to an external or implantable pacemaker, the structures in FIG. 8 associated with delivery of cardioversion/defibrillation pulses can be deleted. Provisions for detection of tachyarrhythmias should be retained if the pacemaker is to provide anti-arrhythmia pacing.

Figure 9:
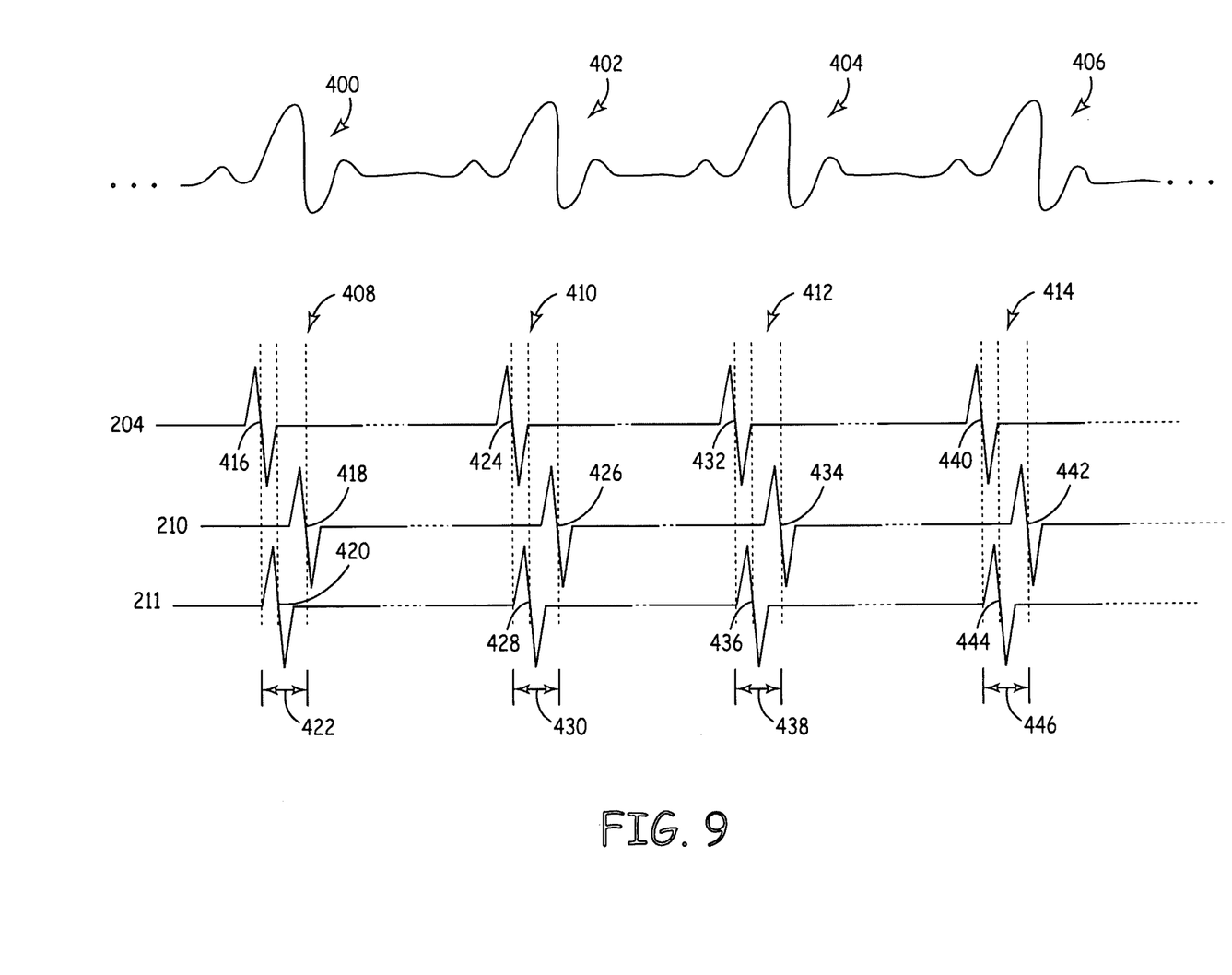
FIG. 9 is a schematic diagram of sensing of depolarization events utilizing a medical device of the present invention.

FIG. 9 is a schematic diagram of sensing of depolarization events utilizing a medical device of the present invention. As illustrated in FIG. 9, during periods of normal depolarization, i.e., periods in which there is proper atrioventricular (AV) conduction resulting in ventricular depolarizations with supraventricular origin, idealized depolarization signals 400-406 are generated as a result of corresponding electrical activity generated through the heart for each depolarization. In a three electrode embodiment of the present invention that includes electrodes 204, 210 and 211 described above, for example, where electrode 204 is positioned within costal muscle 220 along the abdomen below the sternum, electrode 210 is positioned in the anterior thorax, overlaying the heart, slightly left of the sternum and within the fourth intercostal space to be positioned at a location associated the V4 lead of the twelve-lead ECG position, and electrode 211 is positioned laterally left of the sternum from insulated patch 212 to be located at the V6 lead location of the twelve-lead ECG position, a corresponding localized signal 408-414 is sensed by electrodes 204, 210 and 211, respectively, for each depolarization. Each of the sensed localized signals 408-414 includes a respective moment of activation (MOA) of the localized ventricular muscle near the electrode, defined as the zero crossing of the signal. Therefore, localized depolarization 408 includes MOAs 416-420, which occur over detection duration 422, localized depolarization 410 includes MOAs 424-428, which occur over detection duration 430, localized depolarization 412 includes MOAs 432-436, which occur over detection duration 438, and localized detection depolarization 414 includes MOAs 440-444, which occur over detection duration 446.

In this way, as each of the depolarization signals 400-406 propagates through the heart, the propagation is sensed locally at electrodes 204, 210 and 211. Depending upon the electrical activity forming the depolarization event, i.e., whether the depolarization is the result of normal sinus rhythm, a supraventricular event, or a ventricular tachycardia event, and so forth, the sensed localized signals 408-414 are detected in a given sequence and duration that is determined to be characteristic of that event for the particular patient. For example, in the exemplary detection result illustrated in FIG. 9, assuming electrode 204 is identified as a first electrode, electrode 210 is identified as a second electrode, and electrode 211 is identified as a third electrode, and if depolarizations 400-406 are first detected by electrode 204, then by electrode 211, followed by electrode 210, a 1-3-2 detection sequence is generated between electrodes 204, 210 and 211. The detection durations 422, 430, 438, 446, i.e., the duration between the moment of activation of the first electrode to detect the depolarization and the moment of activation of the last electrode to detect the depolarization, remains approximately the same for each local depolarization 408-414. Such a detection sequence and duration may be determined to correspond to normal sinus rhythm, for example. Since this detection sequence and duration represents normal conduction through the patient's heart, it may also represent the patient's normal intrinsic rhythm during atrial fibrillation, or during supraventricular tachycardia such as sinus tachycardia or rapidly conducted atrial fibrillation. Subtle changes in durations 422, 430, 438 and 446 may result from accelerated heart rates during supraventricular tachycardia due to physiologic factors such as increased catecholemine levels, etc.

Figure 10:
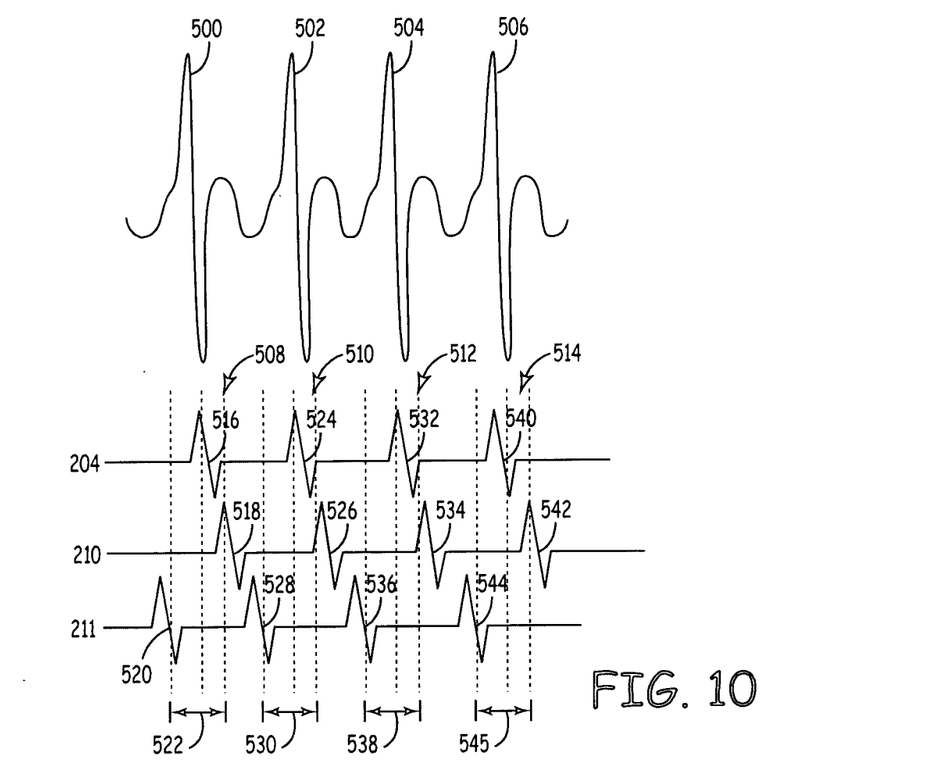
FIGS. 10 and 11 are schematic diagrams of sensing of depolarization events utilizing a medical device of the present invention.
Figure 11:
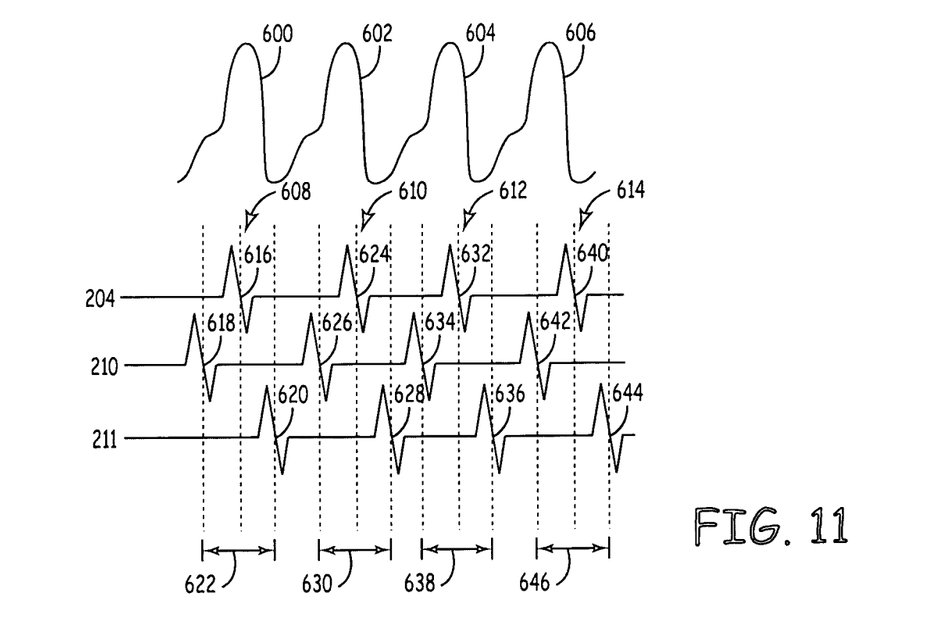

FIGS. 10 and 11 are schematic diagrams of sensing of depolarization events utilizing a medical device of the present invention. As described previously, the detection sequence and duration during supraventricular tachycardia may be similar to the patient's intrinsic rhythm (i.e. normal sinus rhythm), but at a faster heart rate. As illustrated in FIG. 10, a supraventricular tachycardia event may also have conduction aberrancy which results in a detection duration and sequence corresponding to electrodes 204, 210 and 211 which differs from the duration and sequence determine to correspond to normal intrinsic rhythm for that patient. Localized depolarization 508 includes MOAs 516-520, which occur over detection duration 522, localized depolarization 510 includes MOAs 524-528, which occur over detection duration 530, localized depolarization 512 includes MOAs 532-536, which occur over detection duration 538, and localized detection depolarization 514 includes MOAs 540-544, which occur over detection duration 546. The detection durations 522, 530, 538 and 546 may or may not differ relative to the duration 420 associated with normal sinus rhythm, depending upon the patient, but remain approximately the same for each depolarization 500-506.

In the same way, as illustrated in FIG. 11, during a ventricular tachycardia event, depolarizations 600-606 are first detected by electrode 210, then by electrode 204, followed by electrode 211, resulting in a 2-1-3 detection sequence. Localized depolarization 608 includes MOAs 616-620, which occur over detection duration 622, localized depolarization 610 includes MOAs 624-628, which occur over detection duration 630, localized depolarization 612 includes MOAs 632-636, which occur over detection duration 638, and localized detection depolarization 614 includes MOAs 640-644, which occur over detection duration 646. The detection durations 622, 630, 638 and 646 may or may not differ relative to duration 420 associated with normal sinus rhythm or durations 522, 530, 538 and 546 associated with supraventricular tachycardia, depending upon the patient, but remains approximately the same for each depolarization 600-606. During a ventricular fibrillation event, the synchronization of the moment of activations is no longer present, and therefore two significant and relatively easily detectable changes occur with the onset of ventricular fibrillation, namely the sequence of moment of activations and the delays with respect to the other sensor sites change from cycle to cycle for any sensor site, and the event-to-event time or interval between consecutive events varies from beat to beat and from sensor to sensor. Thus, the present invention uses these factors to identify a ventricular fibrillation event.

Figure 12:
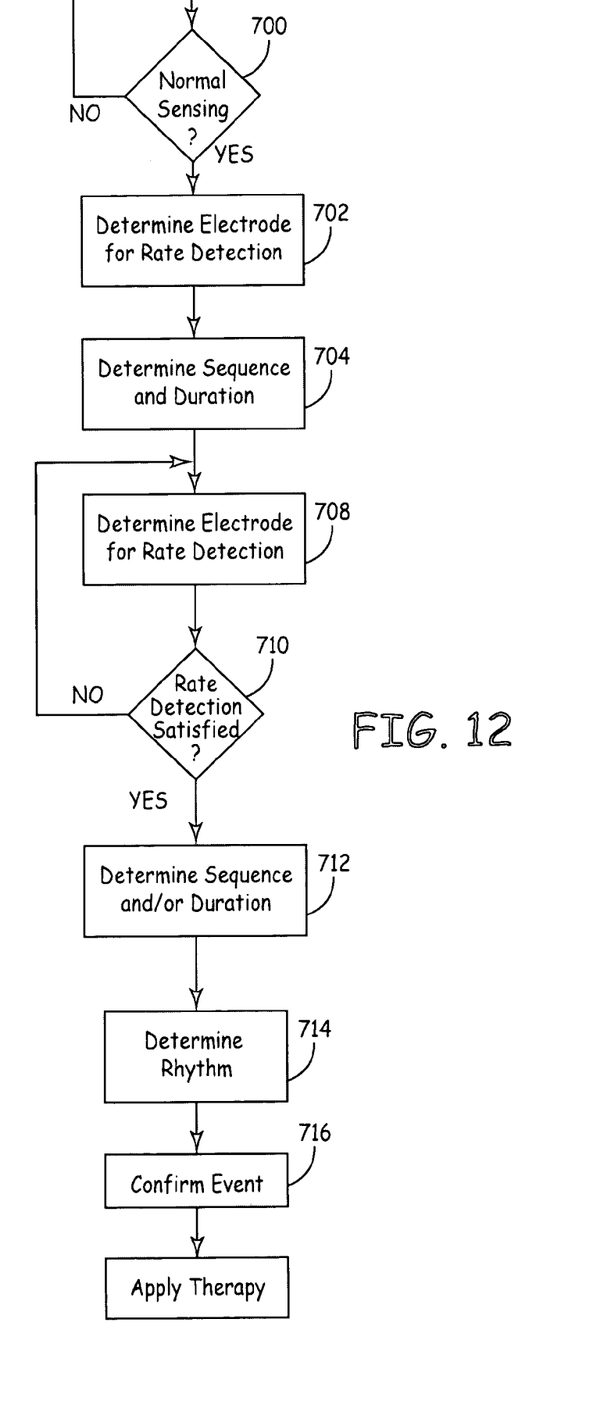
FIG. 12 is a flowchart of a method for detecting arrhythmias in a medical device according to an embodiment of the present invention.

FIG. 12 is a flowchart of a method for detecting arrhythmias in a medical device according to an embodiment of the present invention. As illustrated in FIG. 12, during an initialization period subsequent to placement of device 200 within patient using one of the electrode configurations described above, for example, a determination is made whether normal sensing has been established for each of the electrodes, Step 700, such as electrodes 204, 210 and 211 if the three electrode configuration is utilized. In addition, sensing of cardiac activity may occur between any pair of electrode sub-elements (308, 312, 316) from electrodes 204, 210, 211, or between any electrode sub-elements (308, 312, 316) and any metallic housing or defibrillation electrodes. Such sensing of cardiac activity from non-concentric electrodes provides a more "global" (non-localized) view of cardiac activity than the more localized concentric sensing from electrode 204, 210, and 211. Once normal sensing is established at each electrode, noise levels are determined for each of the electrodes, and, based on the determined noise levels, one of the signals from electrodes 204, 210 and 211 or the global sensing vector (described above) is chosen to be utilized for rate detection, Step 702. As a result, local noise sensed at electrodes resulting from activation of local muscles during intermittent periods of body motion during patient activity can be reduced. Furthermore, since noise due to body motion only intermittently affects the signal quality at an electrode when local muscles are activated, having more than one electrode provides a "redundant" set of cardiac signals that are each affected by muscle noise only during the time when the local muscle is activated, resulting in increased accuracy in sensing cardiac signals.

Once the electrode that is to be utilized for rate detection has been established, the sequences and durations of the sensed signal at the electrodes for normal rhythms, such as normal sinus rhythm or supraventricular tachycardia, are determined, step 704, such as those described above in reference to FIGS. 8 and 9. Using the sequences illustrated in FIGS. 9 and 10, for example, to determine the detection sequences in Step 704, normal sinus rhythm and normal supraventricular tachycardia is identified as being associated with a 1-3-2 detection sequence, and aberrant supraventricular tachycardia is identified as being associated with a 2-3-1 detection sequence between the electrodes 204, 210 and 211. At least one of these normal detection sequences and durations is stored as a "template" by the device for purposes of rhythm classification during future "unknown" fast rate rhythms. Methods for automatically collecting and updating templates of cardiac activity have been previously described in the patent literature, and could be applied in this device to update the detection sequence and durations associated with the patient's normal rhythm. For example, the template generation methods disclosed in commonly assigned U.S. Pat. No. 6,745,068, issued to Koyrakh et al., U.S. patent application Ser. No. 10/826,618 to Cao et al., U.S. patent application Ser. No. 10/826,512 to Cao et al., and U.S. patent application Ser. No. 11/002,482 to Cao et al., all incorporated by reference in their entireties, may be utilized.

After the template of normal rhythm is established, the device is ready to apply the template to the rhythm detection and classification process. Determination of the best signal for rate detection is made by continuously monitoring of all cardiac signals. The cardiac signal with best signal to noise ratio is selected for rate determination among the candidate cardiac signals. Noise levels and signal amplitudes are monitored continuously, and increased noise levels and/or reduced signal amplitudes in the current rate detection sensor are both reasons to potentially change the rate detection signal (step 708). The device continuously monitors the rate detected at the optimum rate detection electrode and determines whether the detected rate meets a predetermined rate detection criterion. The rate detection criterion may consistent of one or more thresholds, such as when the detected rate exceeds a predetermined rate detection threshold, if the detected rate is slower than a predetermined rate detection threshold (indicative of undersensing of the present rhythm or asystole), or if the detected rate becomes highly irregular (also indicative of undersensing of the current rhythm), for example, Step 710. The predetermined detection criterion is programmable, and therefore can be set at any desired set of conditions. According to an embodiment of the present invention, the predetermined rate detection threshold is set to 200 beats per minute, for example, so that an arrhythmia is detected when the detected rate is greater than or equal to 200 beats per minute. Similarly, undersensing may be indicated if the detected rate becomes less than 30 bpm or if the detected rate results in high variability which is indicated by beat-beat variations in detected cardiac intervals of 250 ms or more, or more than some percentage of the patient average heart rate (i.e. beat-to-beat variability of more than 50% of the current heart rate).

If the rate detection criterion are not satisfied, e.g., the detected rate is not irregular, does not exceed the predetermined rate detection threshold, or is not less than the predetermined asystole rate detection threshold, NO in Step 710, a determination is again made as to which electrode is best suited to be chosen to be utilized as the rate detection electrode, Step 708, and the determination of whether the rate detection threshold has been satisfied, Step 710, is repeated using the current selected rate detection electrode.

Once the rate detection criteria are satisfied, Yes in Step 710, the sequence and/or duration of the corresponding signals sensed by the electrodes is determined, Step 712, and, based on the determined sequence and/or duration, the origin of the rhythm is determined, Step 714. In particular, for example, if it is determined that the sequence and/or duration of the current rhythm that meets the rate detection criteria (determined in step 712) is different than the template of normal or aberrant SVT sequence/duration established in step 704, then the appropriate therapy is delivered, such as shock therapy, for example. Beat-to-beat variability of the sequence of activation and/or duration of the current rhythm may indicate a polymorphic rhythm or VF, also indicative of therapy. On the other hand, if it is determined that the sequence and duration established by electrodes 214, 210 and 211 in step 712 is the same as normal or aberrant SVT, then the fast rhythm may be classified as normal and therapy is withheld. Once it is decided to deliver a therapy, the duration and sequences of the events may be used to determine what type of therapy is delivered, such as a pacing therapy or a shock. For example, fibrillatory rhythms may require a shock and will be characterized by disappearance of the synchronization of the MOAs. This may be indicated by the changes in the sequence of MOAs and the delays with respect to the other sensor sites from cycle to cycle for any sensor site and variability of the event-to-event time from beat to beat and from sensor to sensor. On the other hand, rhythms that may be terminated by antitachycardia pacing therapy will demonstrate relative beat-to-beat synchrony of the MOAs.

An additional confirmatory step, 716, may be optionally applied in order to confirm the presence of an arrhythmic event. In particular, rhythms such as fine ventricular fibrillation may be difficult to distinguish from asystole or normal intrinsic rhythm during extended periods (a few cardiac cycles) of noise on one or more of the Laplacian sensors. In order to confirm or refute the presence of a treatable ventricular tachyarrhythmia, one or more pacing pulses could be delivered between two of the sensors, and the cardiac evoked response can be measured by the third electrode/sensor. In asystole, or during electrical noise, there would be a cardiac evoked response but during VF, there wouldn't be a cardiac evoked response. This confirmatory step may or may not be used for rhythms where the activation sequence or duration is consistent from beat-beat, since under these conditions it is more certain that the true rhythm is represented by the electrical events that are being detected, and not corrupted by noise or asystole.

According to an embodiment of the present invention, the change in duration is determined in Step 712 by comparing durations associated with the current rhythm with the durations determined for the determined durations established in Step 704. For example, according to an embodiment of the present invention, the detection duration associated with the current rhythm is compared with the detection duration for normal sinus rhythm that was determined in Step 704, and if the amount that the current detection duration is greater than the normal sinus rhythm duration is less than or equal to a predetermined threshold, the current rhythm is likely a fast rhythm occurring via the normal conduction pattern, and therefore treatment is withheld. If the amount that the current detection duration is greater than the normal sinus rhythm duration is greater than the predetermined threshold, the current rhythm is likely a fast rhythm occurring somewhere other than the normal conduction pattern, and therefore treatment is delivered.

Figure 13:
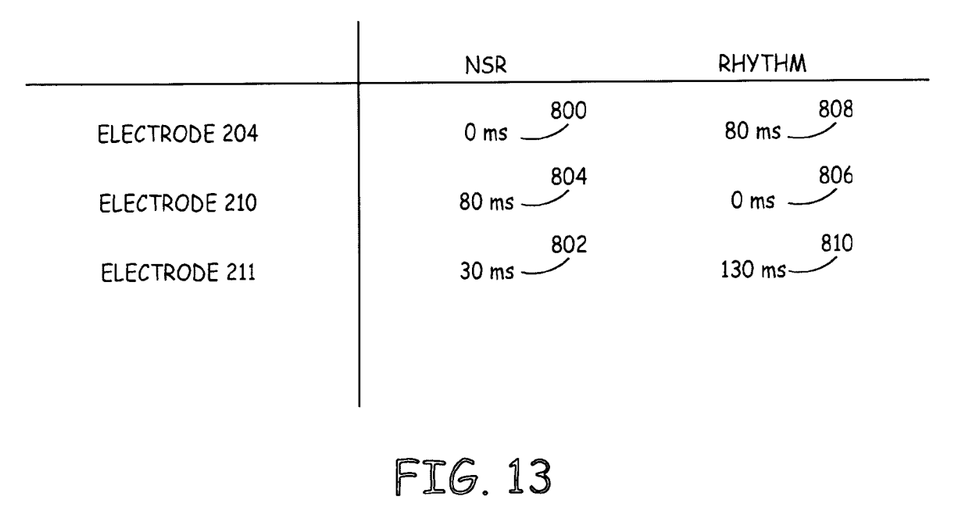
FIG. 13 is an exemplary illustration of determining change in duration for a current rhythm according to an embodiment of the present invention.

FIG. 13 is an exemplary illustration of determining change in duration for a current rhythm according to an embodiment of the present invention. According to an embodiment of the present invention, the detection duration for normal sinus rhythm is classified by identifying the first electrode to detect the rhythm as a reference electrode and setting the reference electrode equal to zero milliseconds. The second and third electrodes are then defined relative to the reference electrode. In particular, as illustrated in FIG. 13, using the exemplary rhythms illustrated in FIGS. 9-11, using the detection sequence associated with electrodes 204, 210 and 211 for normal sinus rhythm as being determined to be a 1-3-2 sequence (FIG. 8), since the first electrode to detect a signal during normal sinus rhythm is electrode 204, followed by electrode 211 and then electrode 210, electrode 204 is set as the reference electrode and is therefore set equal to zero. Since the signal is detected by electrode 211 approximately 30 milliseconds after being detected by the reference electrode (electrode 204) a detection time value for electrode 211 is therefore set equal to 30 milliseconds. In the same way, since the signal is detected by electrode 210 approximately 80 milliseconds after being detected by the reference electrode, a detection time value for electrode 210 is set equal to 80 milliseconds.

In the same way, timing values are assigned for electrodes 204, 210 and 211 during detection of the subsequently sensed rhythm in Step 712 so that the first electrode to sense the current rhythm is set as the reference electrode and therefore set equal to zero and the other two electrodes are then defined relative to the reference electrode. In particular, as illustrated in FIG. 13, since electrode 210 is the first electrode to detect the current rhythm, followed by electrode 204 and then by electrode 211, electrode 210 is set as the reference electrode and is therefore set equal to zero. Since the current rhythm is detected by electrode 204 approximately 80 milliseconds after being detected by the reference electrode (electrode 210), a detection time value for electrode 204 is set equal to 80 milliseconds. In the same way, since the current rhythm is detected by electrode 211 approximately 130 milliseconds after being detected by the reference electrode, a detection time value for electrode 211 is set equal to 130 milliseconds.

It is understood that while a reference point for defining the detection by the electrodes is described in terms of defining the first electrode to detect the rhythm as the reference electrode, other reference points may be utilized. For example, according to an embodiment of the present invention, a peak of a far-field signal detected between two electrodes or between an electrode and the housing of the device, may be utilized as the reference so that the relative times associated with each of the electrodes is defined relative to the detected peak voltage of the far-field signal rather than the first electrode to detect the rhythm locally.

Once the values have been determined for the current rhythm, the sum of the absolute differences of the relative detection time values associated with one of the rhythms determined in Step 704, such as normal sinus rhythm, for example, and the relative detection time values associated with the current rhythm is determined in order to generate a detection duration for the current rhythm. For example, the absolute difference between the relative detection time values associated with electrode 204, i.e., between 0 milliseconds and 80 milliseconds, is determined to be 80 milliseconds, the absolute difference between the relative detection time values associated with electrode 210, i.e., between 80 milliseconds and 0 milliseconds, is determined to be 80 milliseconds, and the absolute difference between the relative detection time values associated with electrode 211, i.e., 30 milliseconds and 130 milliseconds, is determined to be 100 milliseconds, so that the detection duration is determined to be 260 milliseconds (80 ms+80 ms+100 ms), for example.

According to the present invention, the determined detection duration is used to discriminate between cardiac events and is utilized in determining whether to provide therapy and/or the type of therapy to be provided. For example, if the detection duration is determined to be less than or equal to a predetermined threshold, such as 30 ms for example, it is likely that the conduction pattern of the fast rhythm propagates via the normal His-Purkinje system, and therefore no therapy is delivered. However, once the detection duration is substantial, i.e., greater than the predetermined threshold, it is likely that the rhythm is being propagated along a conduction path different from the normal His-Purkinje pathway, such as a cell-to cell conduction pathway that originates in the ventricles. Therefore, it is likely the rhythm is either ventricular tachycardia or supraventricular tachycardia with bundle branch block aberency, and therapy should be delivered.

It is understood that while multiple Laplacian electrodes are illustrated as being utilized above, the present invention could include the use of a single Laplacian sensor and a global sensing in order to provide adequate discrimination. Additional Laplacian electrodes would only serve to improve discrimination accuracy and may not be required.

Figure 14A:
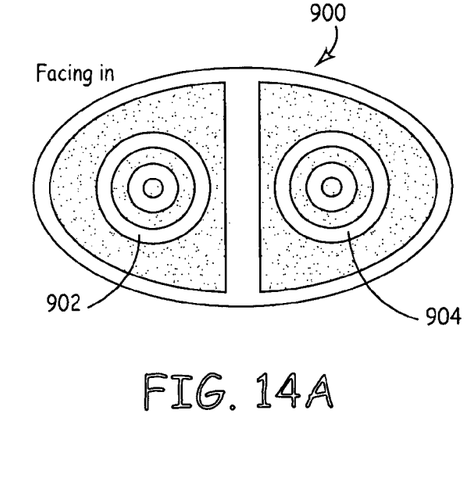
FIGS. 14A-14C are schematic diagrams of electrode configurations in an exemplary medical device according to the present invention.
Figure 14B:
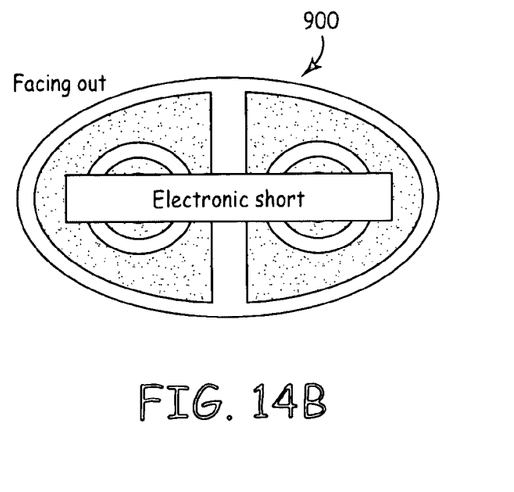
Figure 14C:
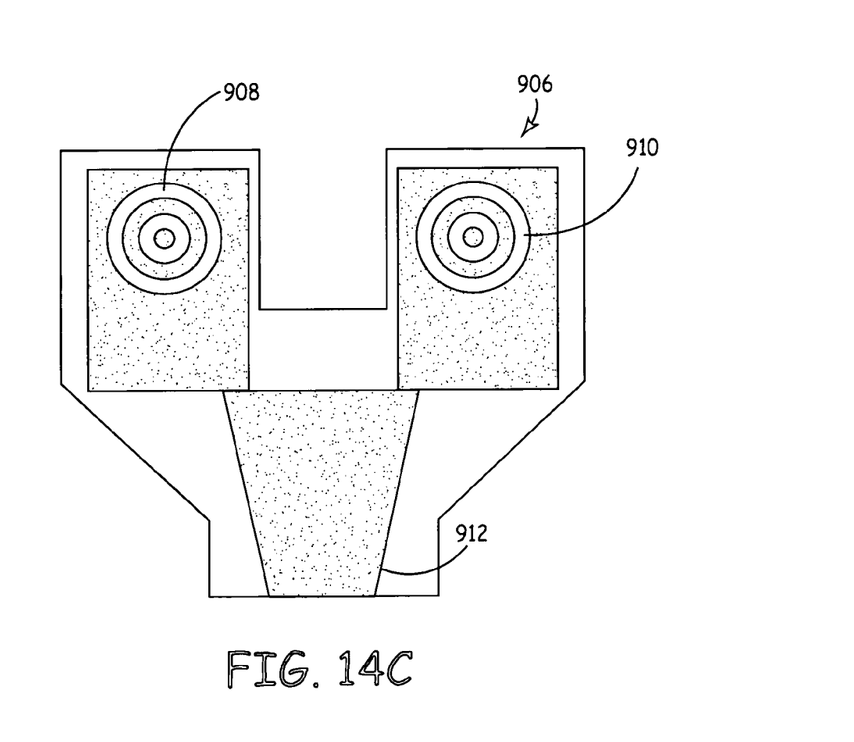

FIGS. 14A-14C are schematic diagrams of electrode configurations in an exemplary medical device according to the present invention. For example, as illustrated in FIGS. 14A and 14B, a patch electrode according to an embodiment of the present invention may include two electrodes 902 and 904, only one of which is utilized as both a sensing and defibrillation electrode. Defibrillation therapy is delivered using both electrodes. According to another embodiment illustrated in FIG. 14C, a patch 906 is formed to integrate one or more Laplacian sensors 908, 910 that are utilized both for sensing and for delivering therapy in combination with a larger surface electrode 912 utilized during defibrillation. For example, the patch could be Y-shaped with a Laplacian electrode at the top ends of the "Y", with the "Y" serving as a cathode and energy would be delivered to an active can which would serve as the anode and also contain a Laplacian electrode. The electrode patch could take any desired shape that enables the use of the larger defibrillation electrode with one or more sensing and defibrillation electrodes.

Some of the techniques described above may be embodied as a computer-readable medium comprising instructions for a programmable processor such as a microprocessor. The programmable processor may include one or more individual processors, which may act independently or in concert. A "computer-readable medium" includes but is not limited to any type of computer memory such as floppy disks, conventional hard disks, CR-ROMS, Flash ROMS, nonvolatile ROMS, RAM and a magnetic or optical storage medium. The medium may include instructions for causing a processor to perform any of the features described above for initiating a session of the escape rate variation according to the present invention.

The preceding specific embodiments are illustrative of the practice of the invention. It is to be understood, therefore, that other expedients known to those of skill in the art or disclosed herein may be employed without departing from the invention or the scope of the appended claim. It is therefore to be understood that the invention may be practiced otherwise than as specifically described, without departing from the scope of the present invention. As to every element, it may be replaced by any one of infinite equivalent alternatives, only some of which are disclosed in the specification.

What is claimed is:

1. A medical device adapted to detect arrythmias in a patient having a thoracic cavity containing a heart generating a cardiac signal comprising a plurality of cardiac events, comprising:
    a plurality of electrodes positionable subcutaneously within the patient and outside of the thoracic cavity sensing the cardiac signal;
    a microprocessor, coupled to the plurality of electrodes:
    identifying a plurality of sequences by which individual ones of the plurality of electrodes sense individual ones of the plurality of cardiac events;
    identifying a plurality of durations comprising time between moments of activation of one of the plurality of electrodes and moments of activation associated with another of said plurality of electrodes;
    determining occurrences of sequence variations in a first sequence of moments of activation associated with a first electrode of the plurality of electrodes and a second sequence of moments of activation associated with a second electrode of the plurality of electrodes, and
    determining occurrences of differences in the durations associated with the moments of activation of the first sequence and the moments of activation of the second sequence, and
    control circuitry delivering a first therapy in response to the occurrences of sequence variations and a second therapy in response to an occurrence of both sequence variations and differences in durations.

2. The device of claim 1, wherein the microprocessor determines whether the sequence is substantially consistent over time and the duration is substantially consistent over time.

3. The device of claim 1, wherein the microprocessor makes a comparison of a change in a duration between individual ones of the plurality of cardiac events to a predetermined threshold, and the control circuitry withholds delivering the therapy in response to the comparison.

4. A medical device adapted to detect arrythmias in a patient having a thoracic cavity containing a heart generating a cardiac signal comprising a plurality of cardiac events, comprising:
    a plurality of electrodes positionable subcutaneously within the patient and outside of the thoracic cavity sensing the cardiac signal;
    a microprocessor, coupled to the plurality of electrodes, identifying:
    a sequence by which individual ones of the plurality of electrodes sense individual ones of the plurality of cardiac events; and
    a duration between sensing by individual ones of the plurality of electrodes of an individual one of the plurality of cardiac events of the cardiac signal; and
    control circuitry delivering a therapy in response to one of the sequence and the duration,
    wherein the microprocessor identifies a first electrode of the plurality of electrodes to detect individual ones of the plurality of cardiac events as a reference electrode, determines relative values corresponding to detection of individual ones of the plurality of cardiac events by a second electrode of the plurality of electrodes to detect the signal and a third electrode of the plurality of electrodes to detect individual ones of the plurality of cardiac events relative to the reference electrode, and generates a detection duration corresponding to the cardiac signal in response to the determined relative values.

5. A method of detecting arrhythmias in a medical device, comprising:
    sensing a cardiac signal comprising a plurality of cardiac events via a plurality of electrodes positioned within a patient and outside of a thoracic cavity of the patient;
    identifying a plurality of sequences of said cardiac signal;
    identifying a plurality of durations comprising time between moments of activation associated with one of the plurality of electrodes and moments of activation associated with another of the plurality of electrodes;

determining occurrences of sequence variations of a first sequence of moments of activation associated with a first electrode of the plurality of electrodes and a second sequence of moments of activation associated with a second electrode of the plurality of electrodes, and determining occurrences of differences in the durations associated with the moments of activation a first one of the plurality of sequences and the moments of activation of a second one of the plurality of sequences, and delivering a therapy comprises delivering a first therapy in response to the occurrences of sequence variations and a second therapy in response to the occurrence of both sequence variations and differences in durations.

6. The method of claim 5, further comprising determining whether the sequence is substantially consistent over time and the duration is substantially consistent over time.

7. The method of claim 5, further comprising:

comparing a change in a duration between cardiac events to a predetermined threshold; and withholding the delivery of the therapy in response to the comparing.

8. A method of detecting arrhythmias in a medical device, comprising:

sensing a cardiac signal comprising a plurality of cardiac events via a plurality of electrodes positioned within a patient and outside of a thoracic cavity of the patient;

identifying a sequence of said cardiac signal;

identifying a duration between sensing by individual ones of the plurality of electrodes of an individual one of the plurality of cardiac events of the cardiac signal; and delivering a therapy in response to one of the sequence and the duration;

comparing a change in the duration between cardiac events to a predetermined threshold by identifying a first electrode of the plurality of electrodes to detect the cardiac events as a reference electrode;

withholding the delivery of the therapy in response to the comparing;

determining a relative detection time corresponding to sensing of the cardiac events;

determining relative values corresponding to detection of the signals by a second electrode of the plurality of electrodes to detect the cardiac events and a third electrode of the plurality of electrodes to detect the cardiac events relative to the reference electrode; and generating a detection duration corresponding to the cardiac events in response to the determined relative values.

* * * * *